US011529387B2

(12) United States Patent
Talbott

(10) Patent No.: US 11,529,387 B2
(45) Date of Patent: Dec. 20, 2022

(54) NUTRITIONAL SUPPLEMENTS AND METHODS OF NUTRITIONAL SUPPLEMENTATION AFFECTING GLOBAL MOOD STATE

(71) Applicant: Amare Global, Irvine, CA (US)

(72) Inventor: Shawn M. Talbott, Draper, UT (US)

(*) Notice: Subject to any disclaimer, the term of this patent is extended or adjusted under 35 U.S.C. 154(b) by 0 days.

(21) Appl. No.: 17/013,319

(22) Filed: Sep. 4, 2020

(65) Prior Publication Data
US 2021/0077560 A1    Mar. 18, 2021

Related U.S. Application Data

(60) Provisional application No. 62/895,919, filed on Sep. 4, 2019.

(51) Int. Cl.
*A61K 36/889* (2006.01)
*A61P 25/00* (2006.01)
*A61K 31/122* (2006.01)
*A23L 33/105* (2016.01)
*A61P 9/00* (2006.01)

(52) U.S. Cl.
CPC .......... *A61K 36/889* (2013.01); *A23L 33/105* (2016.08); *A61K 31/122* (2013.01); *A61P 9/00* (2018.01); *A61P 25/00* (2018.01); *A23V 2002/00* (2013.01)

(58) Field of Classification Search
None
See application file for complete search history.

(56) References Cited

U.S. PATENT DOCUMENTS

| | | | |
|---|---|---|---|
| 7,781,572 B2 | 8/2010 | Bartlett et al. | |
| 7,794,761 B2 | 9/2010 | Shelby et al. | |
| 9,028,890 B2 | 5/2015 | Ferrari et al. | |
| 9,700,071 B2 | 7/2017 | Silver et al. | |
| 10,213,471 B1 | 2/2019 | Buckner | |
| 10,449,148 B2* | 10/2019 | Gutierrez | A61K 31/473 |
| 2003/0206972 A1 | 11/2003 | Babish et al. | |
| 2007/0269541 A1 | 11/2007 | Rohdewald | |
| 2009/0148433 A1 | 6/2009 | Naidu et al. | |
| 2011/0206649 A1 | 8/2011 | Bergonzelli et al. | |
| 2011/0262618 A1 | 10/2011 | Melwitz | |
| 2013/0064803 A1 | 3/2013 | Naidu et al. | |
| 2013/0261183 A1 | 10/2013 | Bhagat | |
| 2016/0000854 A1* | 1/2016 | Osborne | A61K 36/889 424/94.1 |
| 2019/0183849 A1 | 6/2019 | Kariman | |
| 2020/0297605 A1 | 9/2020 | Ambrogio et al. | |
| 2020/0352206 A1 | 11/2020 | Wagner-Salvini | |
| 2020/0397711 A1 | 12/2020 | Lee | |
| 2021/0069280 A1 | 3/2021 | Talbott | |
| 2021/0121490 A1 | 4/2021 | Takahashi et al. | |

FOREIGN PATENT DOCUMENTS

| | | | |
|---|---|---|---|
| CN | 106615516 | * | 5/2017 |
| WO | 03/21515 | A2 | 3/2003 |
| WO | 2014/083438 | A2 | 6/2014 |
| WO | 2015/006646 | A1 | 1/2015 |
| WO | 2015/153841 | A1 | 10/2015 |
| WO | 2018/013871 | A1 | 1/2018 |
| WO | 2018/027070 | A1 | 2/2018 |
| WO | 2018/035212 | A1 | 2/2018 |
| WO | 2018/195097 | A1 | 10/2018 |
| WO | 2019/056129 | A2 | 3/2019 |
| WO | 2019/069096 | A1 | 4/2019 |
| WO | 2019/078005 | A1 | 4/2019 |
| WO | 2019/090273 | A2 | 5/2019 |

OTHER PUBLICATIONS

Ji, X. et al. Astaxanthin Improves Cognitive Performance in Mice . . . Brain Research 1659:88-95, 2017. (Year: 2017).*
Schauss A. Advances in the Study of the Health Benefits and Mechanisms of Action of the Pulp and Seed of the Amazonian Palm Fruit, Euterpe oleracea Mart. Known as Acai. Chapter 10 of Fruits, Vegetables and Herbs, 2016. (Year: 2016).*
Yamashita, E. Let Astaxanthin Be Thy Medicine PharmaNutrition 3:115-122, 2015. (Year: 2015).*
Ambati, R. et al. Astaxanthin: Sources, Extraction, Stability, Biological Activities and its Commercial Applications—A Review. Marine Drugs 12:128-152, 2014. (Year: 2014).*
Kristin Schmidt, Philip J. Cowen, Catherine J. Harmer, George Tzortzis, Steven Errington, Philip W. J. Burnet, Prebiotic intake reduces the waking cortisol response and alters emotional bias in healthy volunteers, 2015, Psychopharmacology, vol. 232, pp. 1793-1801 (Year: 2015).
L.M. Foster, T.A. Tompkins and W.J. Dahl, A comprehensive post-market review of studies on a probiotic product containing Lactobacillus helveticus R0052 and Lactobacillus rhamnosus R0011, 2011, Beneficial Microbes, vol. 2, Issue 4, pp. 319-334 (Year: 2011).
Michael Messaoudi et al., Beneficial psychological effects of a probiotic formulation (Lactobacillus helveticus R0052 and Bifidobacterium longum R0175) in healthy human volunteers, 2011, Gut Microbes, vol. 2, No. 4, pp. 256-261 (Year: 2011).
"International Search Report and Written Opinion of the International Searching Authority," issued in connection with Int'l Appl. No. PCT/US18/48945, dated Nov. 21, 2018 (7 pages).
"International Search Report and Written Opinion of the International Searching Authority," issued in connection with Int'l Appl. No. PCT/US18/48980, dated Nov. 30, 2018 (7 pages).
"International Search Report and Written Opinion of the International Searching Authority," issued in connection with Int'l Appl. No. PCT/US20/49469 dated Dec. 10, 2020 (8 pages).

(Continued)

Primary Examiner — Ralph J Gitomer
(74) Attorney, Agent, or Firm — Holland & Hart LLP

(57) ABSTRACT

Nutritional supplements and methods of nutritional supplementation are described for improving heart and/or brain performance in a subject. The supplements include a combination of astaxanthin and palm fruit extract, and the methods of supplementation include administering to a subject an effective amount of a composition including astaxanthin and palm fruit extract.

19 Claims, 11 Drawing Sheets

(56) References Cited

OTHER PUBLICATIONS

"International Search Report and Written Opinion of the International Searching Authority," issued in connection with Int'l Appl. No. PCT/US20/49545, dated Dec. 10, 2020 (14 pages).

"International Search Report and Written Opinion of the International Searching Authority," issued in connection with Int'l Appl. No. PCT/US20/49555, dated Dec. 21, 2020 (13 pages).

"International Search Report and Written Opinion of the International Searching Authority," issued in connection with Int'l Appl. No. PCT/US20/49560, dated Jan. 7, 2021 (8 pages).

Amare Global, product names Sleep+, p. 2, Key Ingredients, Clinical Study at 2013, https://www.amare.com/corporate/SleepPlus, 1 page; retrieved Feb. 21, 2020.

Frotela-Saseta et al. (2011) Phytother. Res. 25: 1870-1875. (Year: 2011).

Jiang, T. Health Benefits of Culinary Herbs and Spices J of AOAC Int 102(2)395-411 Mar./Apr. 2019. (Year: 2019).

Kapoor et al. (2009) J. Agric. Food Chem. 57: 5358-5364. (Year: 2009).

Kaur et al. (2008) Nutr. Cancer 60(Suppl. 1): 2-11. (Year: 2008).

Kiralan et al. (2014) Industrial Crops and Products 57: 52-58. (Year: 2014).

Ku et al. (2008) Wood Sci. Technol. 42; 47-60. (Year: 2008).

Lizarraga et al. (2007) FEBS Journal 274: 4802-4811. (Year: 2007).

Lotterodt et al. (2010) LWT-Food Science and Technology 43:1409-1413. (Year: 2010).

McGann et al. (2007) Food and Chemical Toxicology 45:1224-1230. (Year: 2007).

Nature's Plus, Ageless Mood Support, title, p. 1, Supplement Facts, Apr. 27, 2015, https://www.amazaon.com/Natrues-Plus-Ageloss-Mood-Support/dp/B00CELG1XI; r1 page, retrieved Feb. 21, 2020.

Radhakrishnan et al. (2011) Frontiers in Bioscience E3, 1509-1523. (Year: 2011).

Raskin et al. (2004) Current Pharmaceutical Design, 10: 3419-3429. (Year: 2004).

Reagan-Shaw et al. (2010) Nutrition and Cancer 62(4): 517-524. (Year: 2010).

Revilla et al. (1998) J. Agric. Food Chem. 46: 4592-4597. (Year: 1998).

Rohdewald (2002) Intern. J. Clin. Pharmacol. Ther. Vol. 40, No. 4: (158-168). (Year: 2002).

Sorndech, W. et al. Isomalto-Oligosaccharides: Recent Insights in Production Technology and Their Use for Food and Medical Applications. Food Science and Technology 95:135-142, 2018. (Year: 2018).

Speranza et al., "Astaxanthin Treatment Reduced Oxidative Induced Pro-Inflammatory Cytokines Secretion in U937: SHP-1 as a Novel Biological Target", Marine Drugs, vol. 20, Issue 4, Apr. 2012, pp. 890-899.

Sreedhar A. et al. Next-Gen Therapeutics for Skin Cancer: Nutraceuticals Nutrition and Cancer 70(5)697-709 Jul. 2019. (Year: 2019).

Talbott et al. "Effect of coordinated probiotic/prebiotic/phytobiotic supplementation on microbiome balance and psychological mood state in healthy stressed adults" Functional Foods in Health and Disease, Apr. 30, 2019; 9(4): 265-275.

Talbott, S. et al. "Effect of Monocot Grass Extract on mood state and sleep patterns in moderately stress subjects", J Int Soc Sports Nutr. 2013, 10 (Suppl 1): p. 26. (Year: 2013).

University of Wisconsin School of Medicine and Health (Non-Pharmaceutical Approaches for Depression Towards Vitality, Pearls for Clinicians, Mar. 12, 2007). (Year: 2007).

Veeriah et al. (2006) Molecular Carcinogenesis 45:164-174. (Year: 2006).

\* cited by examiner

NUTRITIONAL SUPPLEMENTS AND METHODS OF NUTRITIONAL SUPPLEMENTATION AFFECTING GLOBAL MOOD STATE

BACKGROUND

The following relates generally to nutritional supplements and to methods of nutritional supplementation of subjects. More specifically, the following relates to nutritional supplements affecting cardiac and brain performance and to methods of supplementation of subjects in need thereof.

In recent years, researchers have postulated relationships between the cardiovascular and nervous systems. Observations have been made that individuals who suffer from depression have a higher risk of cardiac disorders including heart attacks. Similarly, patients who have suffered from heart attacks or who have undergone heart surgeries are more prone to become depressed. Indeed, the American Heart Association warns heart surgery patients to be aware of symptoms of depression and to advise caretakers of the same because up to 25% of patients suffer "cardiac depression," often after a cardiac event or diagnosis.

Depression is typically treated with a range of different medications, and often with psychotherapy. Many of these medications take some time to alter a patient's symptoms, and many of them have significant side effects that may negatively affect a patient's life. In some cases, patients are hospitalized as symptoms are monitored and medications are adjusted to improve those symptoms over time. Adjusting and transitioning such medications is a difficult, and often lengthy process.

For at least these reasons, there is a need for nutritional supplements and methods of nutritional supplementation to improve heart and brain performance to prevent, improve, reduce, treat or completely relieve patient symptoms. In many cases, there is a need to improve both heart and brain performance and related symptoms concurrently in a patient.

SUMMARY

This description provides improved nutritional supplements and methods of nutritional supplementation to improve both cardiac and psychological parameters in a patient, in some cases concurrently. More specifically, unique nutritional supplements and methods of nutritional supplementation are provided for use with subjects in need of improved heart and brain performance.

A method for simultaneously improving heart and brain performance in a subject is described. The method may include administering to the subject an effective amount of a composition including astaxanthin and palm fruit extract. In some examples of the methods and supplements described herein, the composition may include from about 1 to about 12 mg astaxanthin, and from about 125 to about 500 mg of palm fruit extract. In others, the composition may include from about 3 to about 10 mg astaxanthin, and from about 200 to about 400 mg of palm fruit extract. In still others, the composition may include from about 5 to about 8 mg astaxanthin, and from about 250 to about 350 mg of palm fruit extract.

In some examples of the method, administering to the subject an effective amount of a composition including astaxanthin and palm fruit extract may be conducted for a period of about 4 weeks.

In some examples of the method, administering to the subject an effective amount of a composition including astaxanthin and palm fruit extract may be conducted for a period of greater than 4 weeks.

In some examples of the method, administering to the subject an effective amount of a composition including astaxanthin and palm fruit extract may be conducted for a period of from about 4 weeks to about 8 weeks.

Some examples of the method described herein include the step of identifying a subject in need of improvement of heart and brain performance. This step may, in some instances, include identifying a subject in need of at least one of an increase in aerobic threshold, an increase in anaerobic threshold, an increase in oxidation-reduction potential, an increase in brain-derived neurotrophic factor, an increase in heart rate variability, a reduction of inflammatory markers, an improvement in global mood state, a reduction of depression, and/or a reduction in fatigue. In some examples of the methods disclosed, reduction of inflammatory markers includes reduction of MCP-1, IL-1B, and/or IL-6.

In other aspects, a method for simultaneously improving heart and brain performance in a subject is described. The method may include administering to the subject in need thereof an effective amount of a composition including from about 1 mg to about 12 mg of astaxanthin, and from about 125 mg to about 500 mg of palm fruit extract, where the composition is administered to the subject for a period of 4 weeks. In some variants, the administration is conducted for a period of at least about 4 weeks.

In some examples of the method, the composition may include from about 3 to about 10 mg astaxanthin, and from about 200 to about 400 mg of palm fruit extract.

In some examples of the method, the composition may include from about 5 to about 8 mg astaxanthin, and from about 250 to about 350 mg of palm fruit extract.

In some examples of the method, administering to the subject an effective amount of a composition including astaxanthin and palm fruit extract may be conducted for a period of from about 4 weeks to about 8 weeks.

In some examples of the method described herein, administering to the subject an effective amount of a composition including astaxanthin and palm fruit extract may be conducted for a period of greater than 4 weeks.

Some examples of the methods described herein further include identifying a subject in need of improvement of heart and brain performance. This may include identifying a subject in need of at least one of an increase in aerobic threshold, an increase in anaerobic threshold, an increase in oxidation-reduction potential, an increase in brain-derived neurotrophic factor, an increase in heart rate variability, a reduction in inflammatory markers, an improvement in global mood state, a reduction of depression, and/or a reduction in fatigue. In some examples of the method, a reduction in inflammatory markers may include a reduction in MCP-1, IL-1B, and/or IL-6.

Still further, methods for simultaneously improving heart and brain performance in a subject are described. The methods may include identifying a subject in need of improvement of heart and brain performance, administering to the subject in need thereof an effective amount of a composition including from about 1 mg to about 12 mg of astaxanthin, from about 125 mg to about 500 mg of palm fruit extract, and continuing to administer the composition to the subject for a period of from about 4 weeks to about 8 weeks.

In some examples of the methods described herein, identifying a subject in need of improvement of heart and brain performance may include identifying a subject in need of at least one of increase in aerobic threshold, increase in anaerobic threshold, increase in oxidation-reduction potential, increase in brain-derived neurotrophic factor, increase in heart rate variability, reduction in inflammatory markers, improvement in global mood state, reduction of depression, and/or reduction in fatigue.

DETAILED DESCRIPTION

Figure 1:
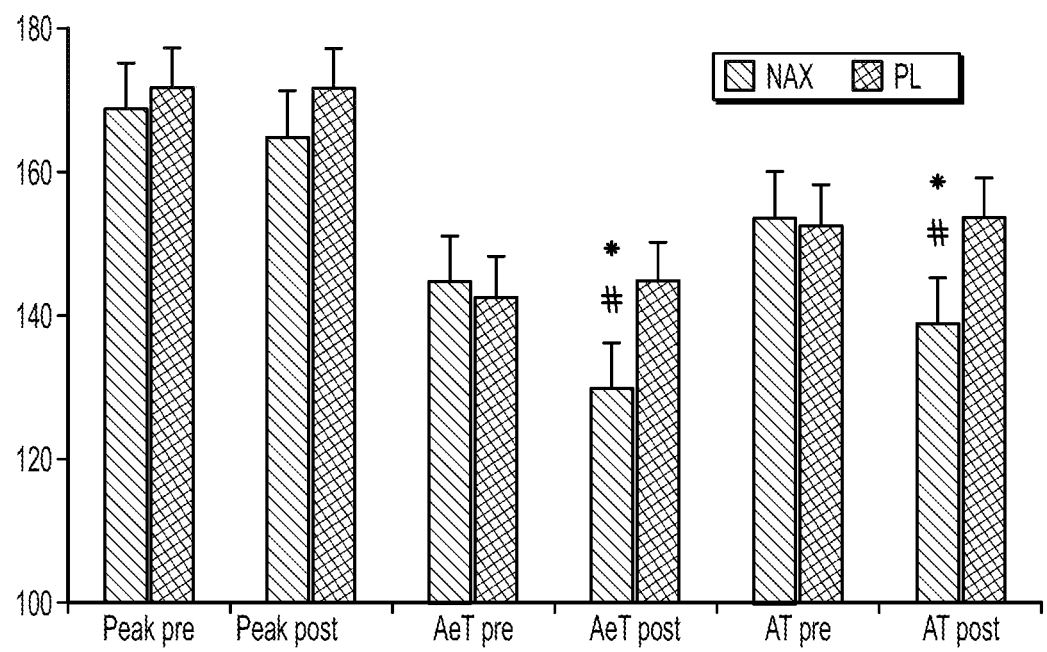
FIG. 1 is a table reporting the effect of astaxanthin supplementation on aerobic and anaerobic threshold in runners supplemented with astaxanthin.

This application discloses novel compositions useful as nutritional supplements for supplementing the nutrition of patients to improve both heart and brain performance and health. It further discloses methods of supplementation of subjects to improve heart and brain performance. In at least some of the compositions and methods disclosed, the improvements in heart/cardiac health and brain health may occur, or may be observed to occur, concurrently.

Ongoing studies and research are being conducted to explore the apparent link between heart health and brain health. As this field progresses, there is a need for methods and related supplement formulations to support a patient's cardiac and brain health. In some instances, it would be beneficial to have methods and supplement formulations that supported and improved cardiac and brain health at the same time, simplifying patient care and providing a unique approach to supporting health and reducing patient suffering.

As used herein, treatment means any manner in which the symptoms or pathology of a condition, disorder or disease are ameliorated or otherwise beneficially altered. Treatment also encompasses any pharmaceutical use of the compositions herein.

The supplement compositions of the present disclosure may be administered in a variety of suitable dosage forms, including, without limitation, tablets, capsules, granules, powders, liquids, liposome inclusions, ointments, gels, external powders, sprays, inhalable powders, injectable preparations (solutions, suspensions, emulsions, solids to be dissolved when used, etc.), eye drops, eye ointments, suppositories, and the like can be selected appropriately depending on the administration method, and the compositions of the present disclosure can be accordingly formulated. Formulation in general is described in references including Comprehensive Medicinal Chemistry, Volume 5, Editor Hansch et al, Pergamon Press 1990.

As used herein, any range set forth is inclusive of the end points of the range unless otherwise stated.

As used herein, "effective amount" refers to an amount of a substance which is sufficient to achieve its intended purpose or effect. Various biological factors may affect the ability of a delivered substance to perform its intended task. Therefore, an "effective amount" may be dependent on such biological factors. An effective amount of a compound for treating a disorder is an amount that is sufficient to ameliorate, or in some manner reduce a symptom or stop or reverse progression of a condition. Such amount may be administered as a single dosage or may be administered according to a regimen whereby it is effective. The achievement of therapeutic effects may be measured by a physician or other qualified medical personnel using evaluations known in the art, (for example with testosterone supplementation therapy, physical examination, blood and saliva tests may be used), it is recognized that individual variation and response to treatments may make the achievement of therapeutic effects a subjective decision.

As used herein, "administration," and "administering" may be used interchangeably, and refer to the act of presenting, applying, or introducing a drug to a subject in order to achieve a desired physiological or psychological response.

As used herein, amelioration of the symptoms of a particular disorder by administration of a particular pharmaceutical composition refers to any lessening, whether permanent or temporary, lasting or transient that can be attributed to or associated with administration of the composition.

Thus, according to the present disclosure, methods for simultaneously improving heart and brain performance in a subject are described. The methods may include administering to the subject an effective amount of a composition including astaxanthin and palm fruit extract. In some examples of the methods and supplements described herein, the composition may include from about 1 to about 12 mg astaxanthin, and from about 125 to about 500 mg of palm fruit extract. In others, the composition may include from about 3 to about 10 mg astaxanthin, and from about 200 to about 400 mg of palm fruit extract. In still others, the composition may include from about 5 to about 8 mg astaxanthin, and from about 250 to about 350 mg of palm fruit extract.

In some examples of the method, administering to the subject an effective amount of a composition including astaxanthin and palm fruit extract may be conducted for a period of greater than 4 weeks.

In some examples of the method, administering to the subject an effective amount of a composition including astaxanthin and palm fruit extract may be conducted for a period of greater than 4 weeks.

In some examples of the method, administering to the subject an effective amount of a composition including astaxanthin and palm fruit extract may be conducted for a period of from about 4 weeks to about 8 weeks.

Some examples of the method described herein include the step of identifying a subject in need of improvement of heart and brain performance. This step may, in some instances, include identifying a subject in need of at least one of an increase in aerobic threshold, an increase in anaerobic threshold, an increase in oxidation-reduction potential, an increase in brain-derived neurotrophic factor, an increase in heart rate variability, a reduction of inflammatory markers, an improvement in global mood state, a reduction of depression, and/or a reduction in fatigue. In some examples of the methods disclosed, reduction of inflammatory markers includes reduction of MCP-1, IL-1B, and/or IL-6.

In other aspects, a method for simultaneously improving heart and brain performance in a subject is described. The method may include administering to the subject in need thereof an effective amount of a composition including from about 1 mg to about 12 mg of astaxanthin, and from about 125 mg to about 500 mg of palm fruit extract, where the composition is administered to the subject for a period of at least about 4 weeks.

In some examples of the method, the composition may include from about 3 to about 10 mg astaxanthin, and from about 200 to about 400 mg of palm fruit extract.

In some examples of the method, the composition may include from about 5 to about 8 mg astaxanthin, and from about 250 to about 350 mg of palm fruit extract.

In some examples of the method, administering to the subject an effective amount of a composition including astaxanthin and palm fruit extract may be conducted for a period of from about 4 weeks to about 8 weeks.

In some examples of the method described herein, administering to the subject an effective amount of a composition including astaxanthin and palm fruit extract may be conducted for a period of greater than 4 weeks.

Some examples of the methods described herein further include identifying a subject in need of improvement of heart and brain performance. This may include identifying a subject in need of at least one of an increase in aerobic threshold, an increase in anaerobic threshold, an increase in oxidation-reduction potential, an increase in brain-derived neurotrophic factor, an increase in heart rate variability, a reduction in inflammatory markers, an improvement in global mood state, a reduction of depression, and/or a reduction in fatigue. In some examples of the method, a reduction in inflammatory markers may include a reduction in MCP-1, IL-1B, and/or IL-6.

Still further, methods for simultaneously improving heart and brain performance in a subject are described. The methods may include identifying a subject in need of improvement of heart and brain performance, administering to the subject in need thereof an effective amount of a composition including from about 1 mg to about 12 mg of astaxanthin, from about 125 mg to about 500 mg of palm fruit extract, and continuing to administer the composition to the subject for a period of from about 4 weeks to about 8 weeks.

In some examples of the methods described herein, identifying a subject in need of improvement of heart and brain performance may include identifying a subject in need of at least one of increase in aerobic threshold, increase in anaerobic threshold, increase in oxidation-reduction potential, increase in brain-derived neurotrophic factor, increase in heart rate variability, reduction in inflammatory markers, improvement in global mood state, reduction of depression, and/or reduction in fatigue.

The mood state and psychological/brain benefits of the cardiovascular improvements are completely novel and unexpected (at any level of ingredient usage).

Figure 2:
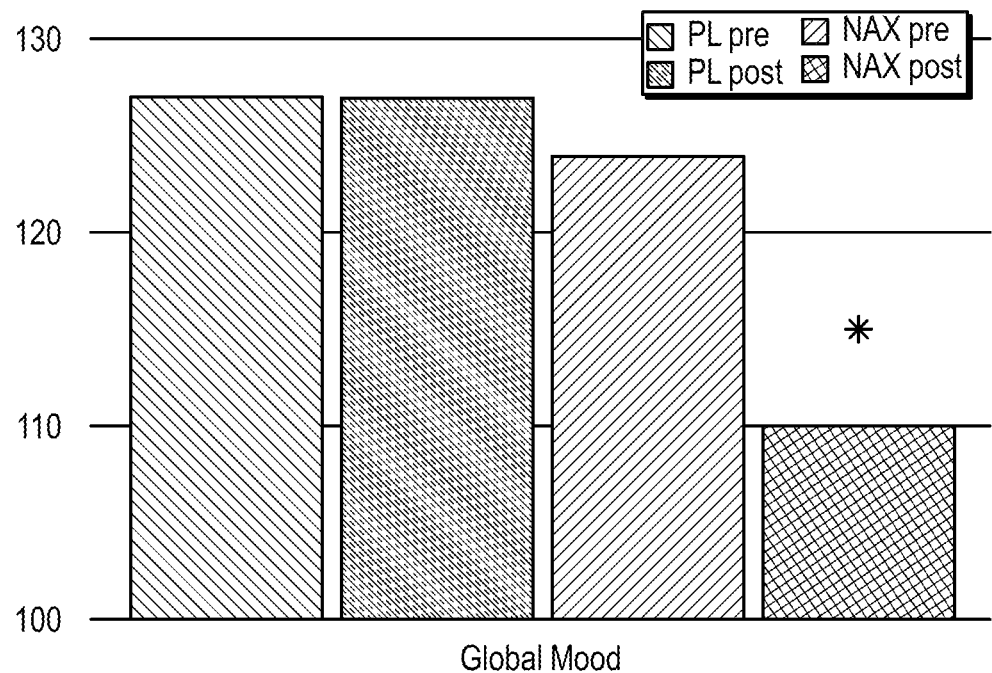
FIG. 2 is a table reporting global mood state pre- and post-supplementation with astaxanthin.
Figure 3:
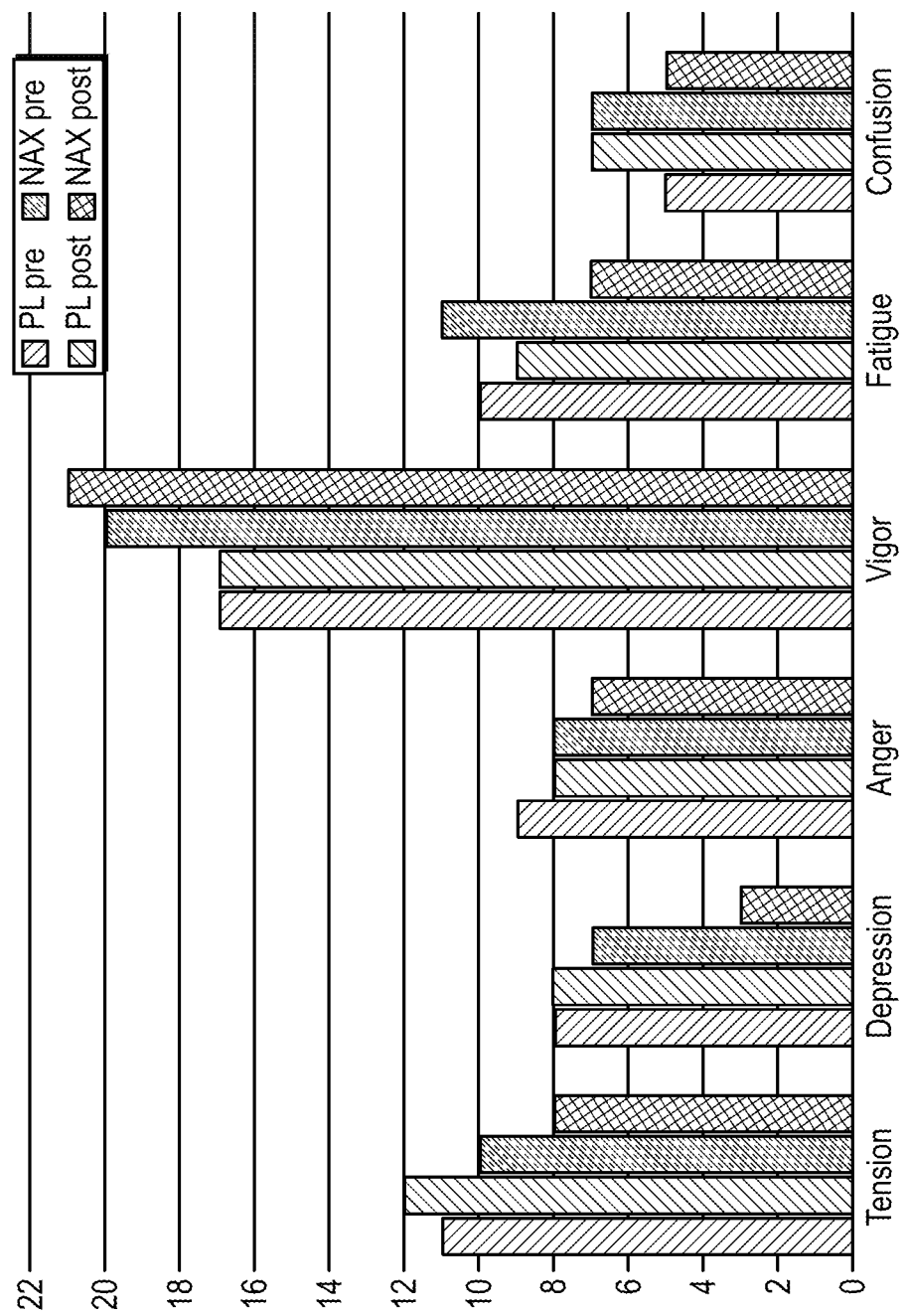
FIG. 3 is a table reporting the effects of astaxanthin supplementation on psychological mood state in healthy subjects.
Figure 4:
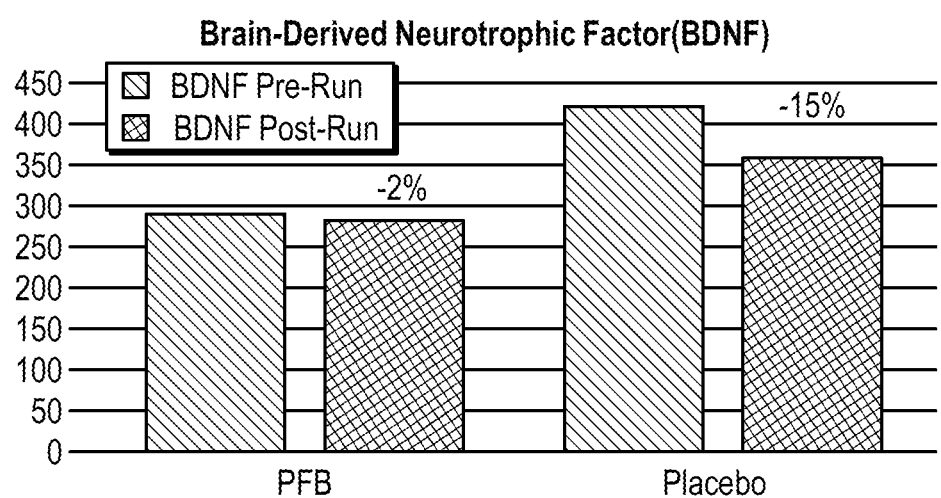
FIG. 4 is a table reporting the effect of exercise on brain-derived neutrophic factor ("BDNF") with and without PFB—palm fruit extract.
Figure 5:
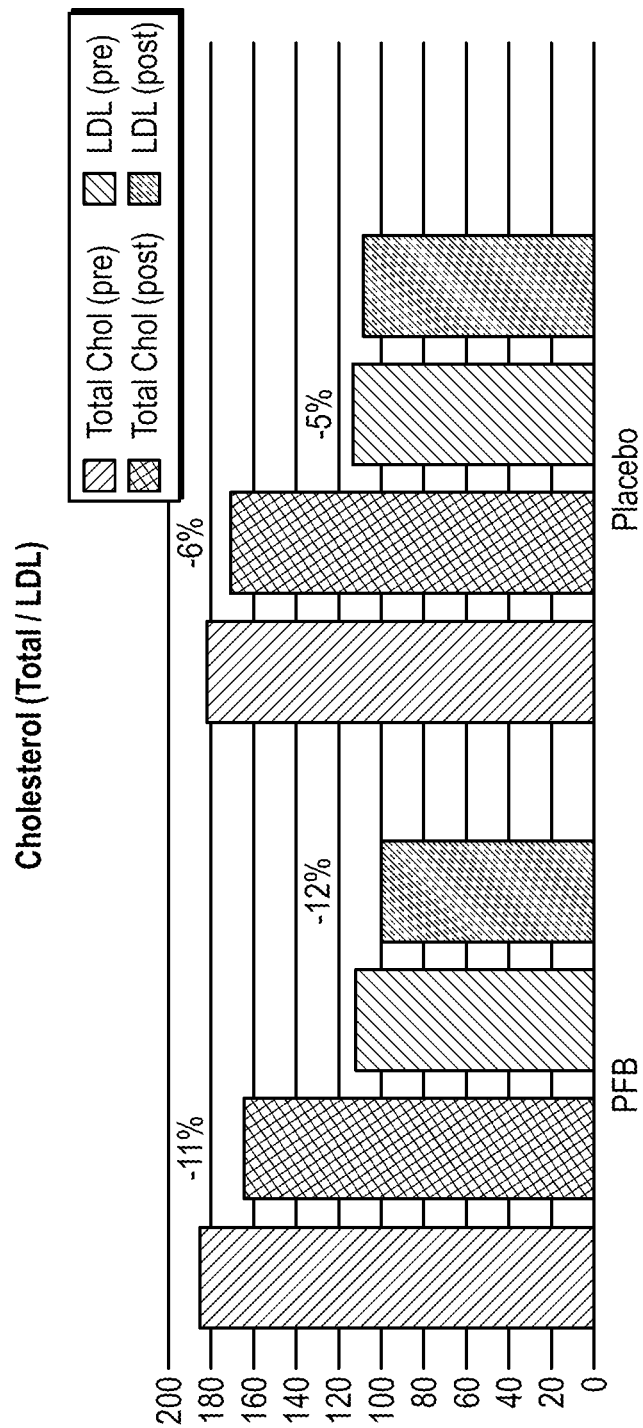
FIG. 5 is a table reporting the effect on total and LDL cholesterol levels of PFB supplementation versus a placebo.
Figure 6:
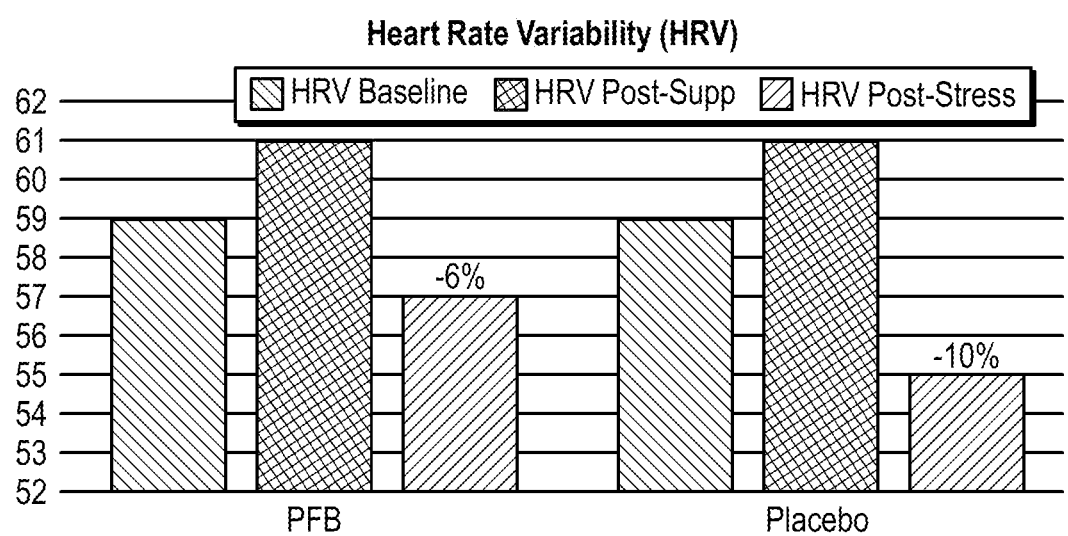
FIG. 6 is a table reporting the effect of PFB supplementation on heart rate variability.
Figure 7:
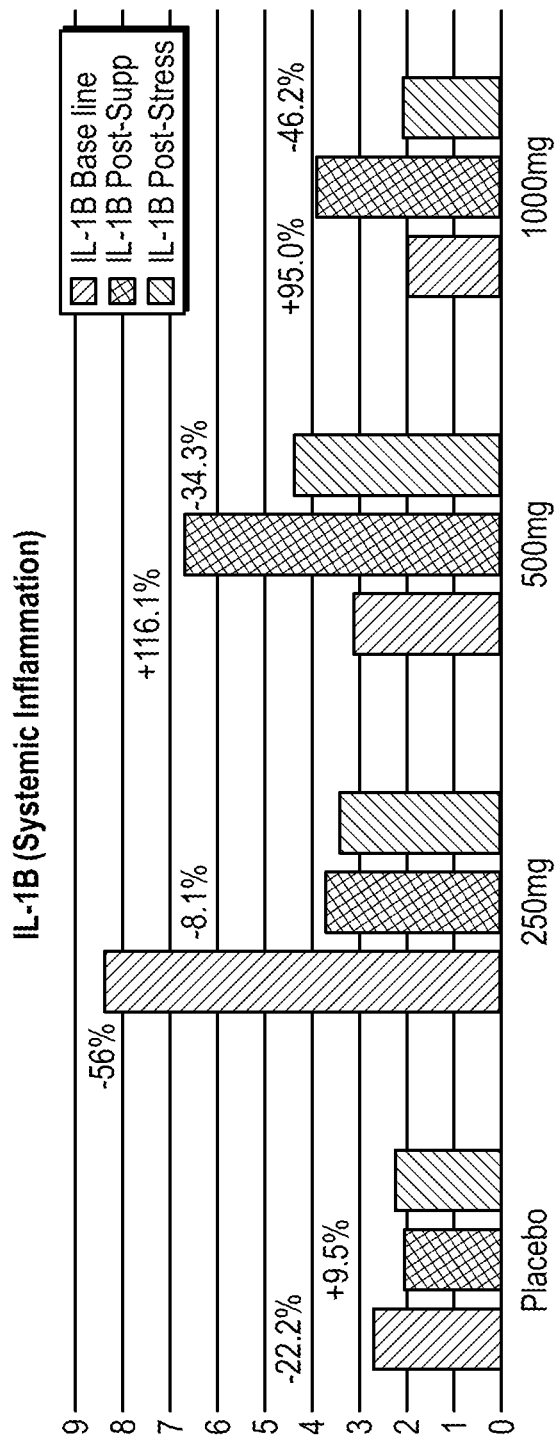
FIG. 7 is a table reporting the effect of PFB supplementation on stress-induced inflammation versus a placebo.
Figure 8:
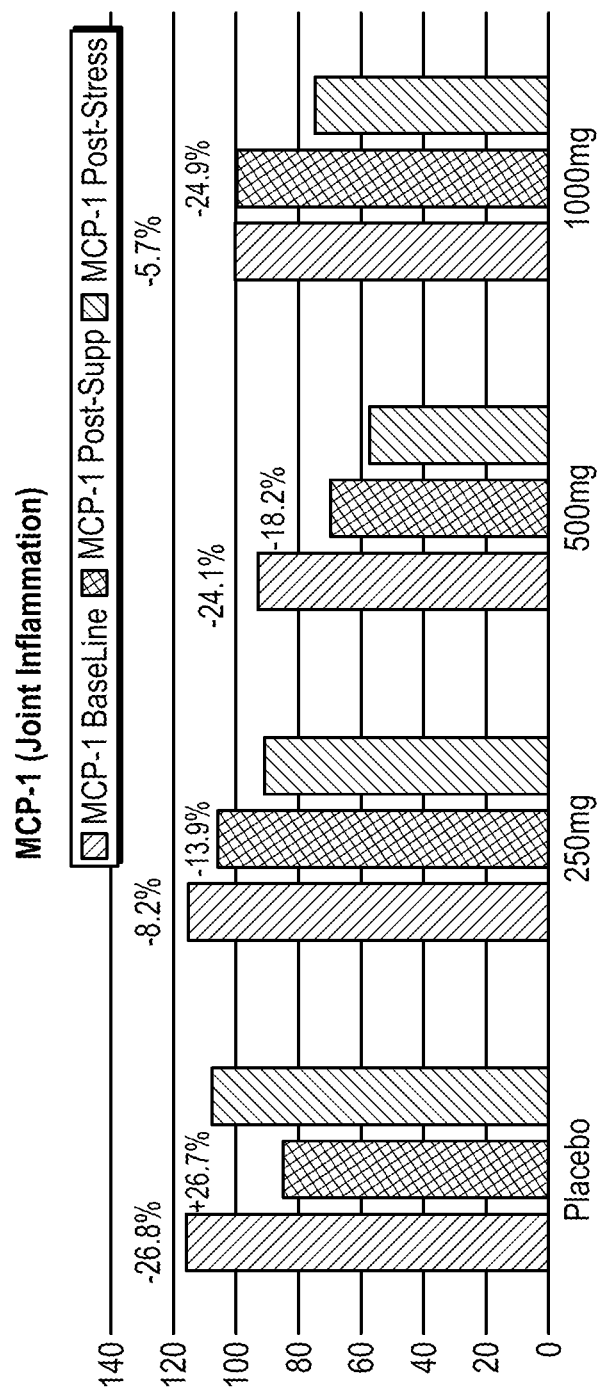
FIG. 8 is a table reporting the effect of PFB supplementation on stress-induced inflammation versus a placebo.
Figure 9:
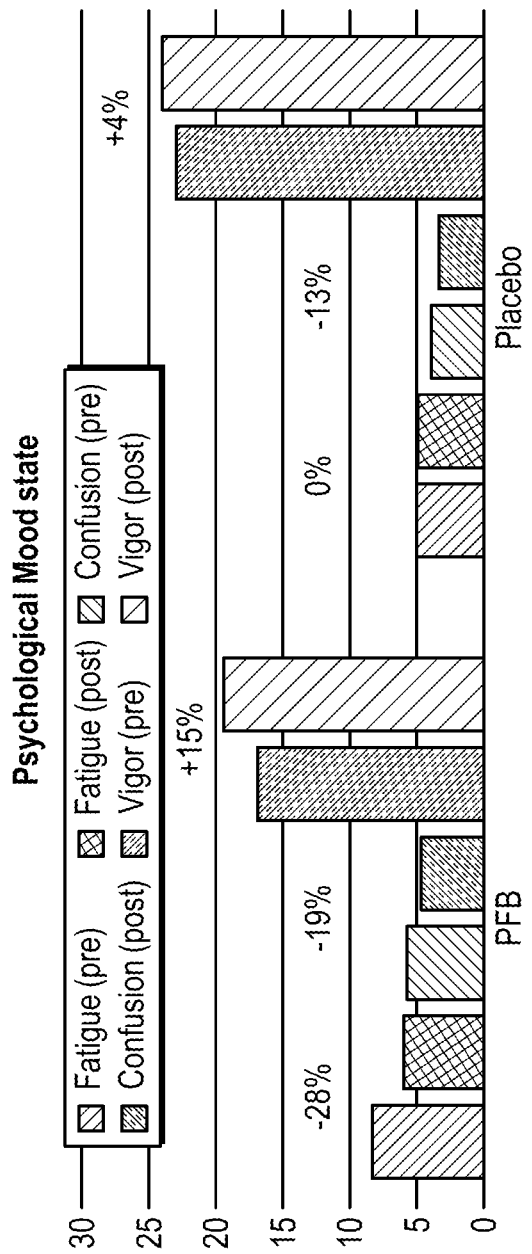
FIG. 9 is a table reporting the effect of PFB supplementation on psychological mood state, as measured by POMS "Profile of Mood States" psychological rating scale.

FIG. 1 is a table reporting the effect of astaxanthin supplementation on aerobic and anaerobic threshold in runners supplemented with astaxanthin, illustrating heart rate at baseline (pre-supplementation) and week 8 (post-supplementation). At submaximal running intensity (AeT, aerobic threshold and AT, anaerobic threshold), the NAX group had significantly lower heart rate (HR) compared to pre-supplementation values (*) and compared to placebo (PL)values (#, both p<0.05) (Talbott., et al. "Effect of Astaxanthin Supplementation on Cardiorespiratory Function in Runners". EC Nutrition 11.6 (2016): 253-259;

FIG. 2 is a table reporting global mood state pre- and 8 weeks post-supplementation with astaxanthin. Improvements were found in NAX for Global Mood (−11%, NAX=127+20 v. PL=127+20; p<0.05).*A lower score for Global Mood State indicates a more positive psychological mood state (Talbott et al. "Astaxanthin Supplementation Reduces Depression and Fatigue in Healthy Subjects." EC Nutrition 14.3 (2019): 239-246);

FIG. 3 is a table reporting the effects of astaxanthin supplementation on psychological mood state in health subjects, presenting psychological mood state sub-scales at baseline (pre-supplementation) and week 8 (post-supplementation). Improvements were found in NAX for some mood state subscales: Tension (−20%, NS), Depression (−57%, p<0.05), Anger (−12%, NS), Vigor (+5%, NS), Fatigue (−36%, p<0.05), and Confusion (−28%, NS) (Talbott et al. "Astaxanthin Supplementation Reduces Depression and Fatigue in Healthy Subjects." EC Nutrition 14.3 (2019): 239-246);

FIG. 4 is a table reporting the effect of exercise on brain-derived neutrophic factor ("BDNF") with and without PFB—palm fruit extract. BDNF levels fall in response to exercise stress (−15% in Placebo)—which is prevented by PFB (−2%). Low BDNF suggests reduced neuroplasticity and predisposes to depression;

FIG. 5 is a table reporting the effect on total and LDL cholesterol levels of PFB supplementation versus a placebo. Total cholesterol levels dropped by more in PFBc group (−11%) compared to Placebo (−6%). LDL cholesterol levels dropped by more in PFBc group (−12%) compared to Placebo (−5%);

FIG. 6 is a table reporting the effect of PFB supplementation on heart rate variability (HRV). Exercise stress reduced HRV by 10% indicating inadequate recovery from stress). PFB supplementation appeared to attenuate the reduction in HRV (−6%)—suggesting improved cardiac resilience to stress;

FIG. 7 is a table reporting the effect of PFB supplementation on stress-induced inflammation versus a placebo. Running challenge ("stress") increased inflammation (+9.5% Placebo), which was dose-dependently reduced by PFBc);

FIG. 8 is a table reporting the effect of PFB supplementation on stress-induced inflammation versus a placebo. Four weeks of run training reduces joint inflammation in all groups (no effect of PFBc supplementation). But "racing" induces "stress" and increases joint inflammation (+26.7%), which is prevented dose-dependently by PFB);

FIG. 9 is a table reporting the effect of PFB supplementation on psychological mood state, as measured by POMS "Profile of Mood States" psychological rating scale. PFB supplementation improved Psychological Mood State compared to Placebo. There was 28% less fatigue in PFBc (vs.

0% in Placebo), 19% less confusion in PFBc (vs. −13% in Placebo) and a 15% increase in vigor in PFBc vs.+4% in Placebo.

Example 1

Experimental Design

A study was conducted to explore the effects of supplementation using supplements and methods of supplementation according to the present disclosure. A test group of 60 health adult subjects, including 30 men and 30 women were recruited to participate in the study. The subjects averaged 45 years of age, with a range of from 20-66 years old.

The study subjects underwent nutritional supplementation with a nutritional supplement. The supplement included between about 4 and about 12 mg of astaxanthin and between about 250 to about 1,000 mg of palm fruit extract/PFB. Supplementation was conducted for a period of 4-8 weeks.

Several physiological and fitness level parameters were measured at the beginning of the study, including aerobic threshold, anaerobic threshold, oxidation-reduction potential, brain-derived neurotrophic factor, heart rate variability, and inflammatory marker levels. Baseline measurements of global mood state, depression and fatigue were also taken.

Subjects of the study received the supplement once-daily for a period of 4-8 weeks, following which aerobic threshold, anaerobic threshold, oxidation-reduction potential, brain-derived neurotrophic factor, heart rate variability, and inflammatory marker levels were measured again. Study end measurements of global mood state, depression and fatigue were also taken.

The results of the study are indicated below as averages:

TABLE 1

| Research Study Results | |
| --- | --- |
| Aerobic Threshold: | +10% improvement |
| Anaerobic Threshold: | +10% improvement |
| Oxidation-Reduction Potential: | +140% improvement |
| Brain-Derived Neurotrophic Factor: | +22% improvement |
| Inflammatory Markers: | −45% MCP-1 |
|  | −40% IL-1B |
|  | −104% IL-6 |
| Global Mood State: | +11% |
| Depression: | −57% |
| Fatigue: | −36% |

Study subjects showed 10% improvements in both aerobic and anaerobic threshold, as well as 140% improvement in oxidation-reduction potential. This improvement oxidation-reduction potential indicates an increase in cellular protection and antioxidant protection. Subjects further exhibited a 22% improvement in brain-derived neurotrophic factor, which indicates potential for increased neuron growth and repair. This is also regarded as a proxy for improved general brain health. In addition, subjects demonstrated a 30% improvement in heart rate variability, indicating a decrease in cardiac stress. The decreases in three inflammatory markers (MCP-1, IL-1B and IL-6) reported also suggest broad heart and brain benefits to the study subjects.

In addition to the physiological benefits reported above, study subjects reported increased (11%) global mood state with significant decreases in both depression (−57%) and fatigue (−36%).

Figure 10:
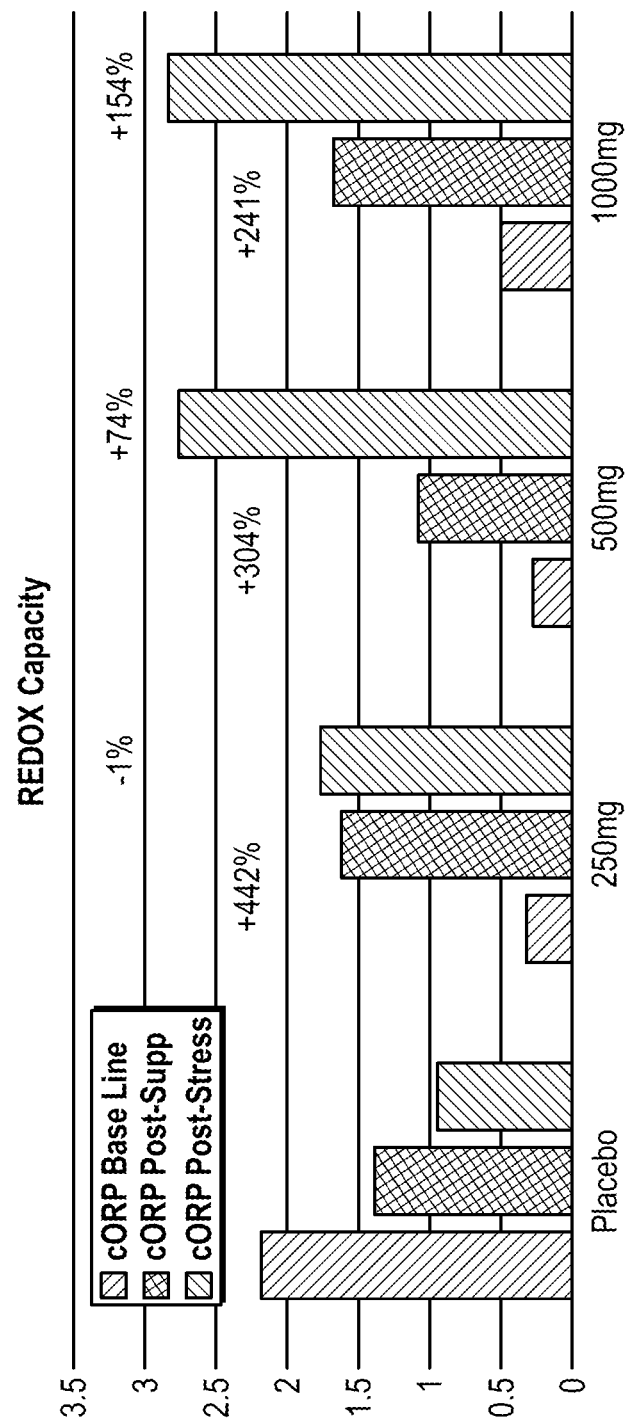
FIG. 10 is a table reporting the effect of supplementation with astaxanthin and PFB, as disclosed herein, on REDOX capacity.
Figure 11:
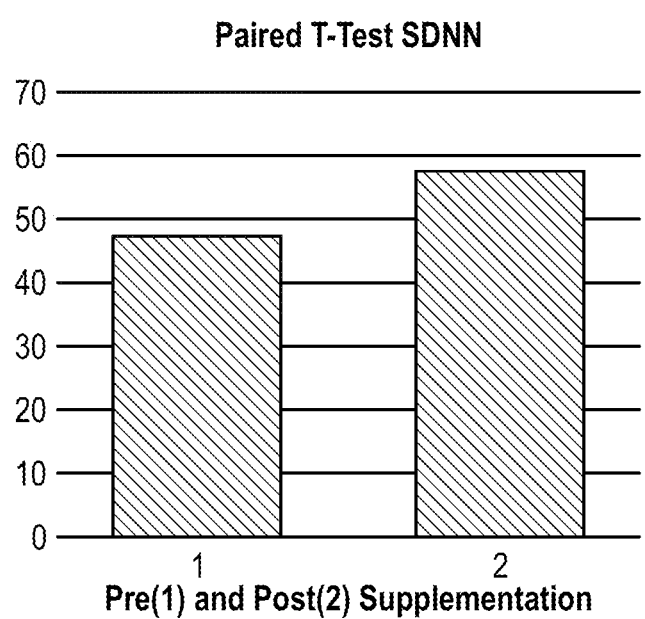
FIG. 11 is a table reporting the effect of supplementation with astaxanthin and palm fruit extract on heart rate variability.

In addition, as shown in FIG. 10, subjects showed a 22% improvement in heartrate variability post-supplementation with PFB and astaxanthin, as taught herein. Subjects also saw similar improvements in POMS/mood data as in the earlier FIGS. shown above. REDOX capacity is enhanced 2-4 fold by PFBc supplementation, and REDOX capacity is reduced by exercise stress (−32%, Placebo), but further enhanced by PFBc.

It should be noted that the methods described herein describe possible implementations, and that the operations and the steps may be rearranged or otherwise modified and that other implementations are possible. Further, aspects from two or more of the methods may be combined.

As used herein, including in the claims, "or" as used in a list of items (e.g., a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label, or other subsequent reference label.

The description set forth herein, in connection with the appended figures, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

All patent applications, patents and publications cited in this specification are hereby incorporated by reference in their entirety. In the case of inconsistencies, the present disclosure, including definitions, will prevail.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method of simultaneously improving heart and brain performance in a subject comprising:
    administering to the subject an effective amount of a composition comprising:
        astaxanthin; and
        palm fruit extract, wherein:
the effective amount is effective to simultaneously improve heart and brain performance in the subject and
the effective amount is effective to improve global mood state in the subject.

2. The method of claim 1, wherein the composition comprises:
from about 1 to about 12 mg astaxanthin; and
from about 125 to about 500 mg of palm fruit extract.

3. The method of claim 2, wherein the composition comprises:
from about 3 to about 10 mg astaxanthin; and
from about 200 to about 400 mg of palm fruit extract.

4. The method of claim 3, wherein the composition comprises:
from about 5 to about 8 mg astaxanthin; and
from about 250 to about 350 mg of palm fruit extract.

5. The method of claim 1, wherein administering to the subject an effective amount of a composition comprising astaxanthin and palm fruit extract is conducted for a period of greater than 4 weeks.

6. The method of claim 1, wherein administering to the subject an effective amount of a composition comprising astaxanthin and palm fruit extract is conducted for a period of from about 4 weeks to about 8 weeks.

7. The method of claim 1, further including the step of identifying a subject in need of improvement of heart and brain performance.

8. The method of claim 7, wherein identifying a subject in need of improvement of heart and brain performance includes identifying a subject in need of improvement in global mood state.

9. The method of claim 1, wherein the effective amount is effective to reduce a MCP-1, IL-1B, and/or IL-6 concentration in the subject.

10. A method of simultaneously improving heart and brain performance in a subject comprising:
administering to the subject in need thereof an effective amount of a composition comprising:
from about 1 mg to about 12 mg of astaxanthin;
from about 125 mg to about 500 mg of palm fruit extract; and
wherein:
the composition is administered to the subject for a period of at least about 4 weeks,
the effective amount is effective to simultaneously improve heart and brain performance in the subject following administration for the period of at least about 4 weeks; and
the effective amount is effective to improve global mood state in the subject following administration for the period of at least about 4 weeks.

11. The method of claim 10, wherein the composition comprises:
from about 3 to about 10 mg astaxanthin; and
from about 200 to about 400 mg of palm fruit extract.

12. The method of claim 11, wherein the composition comprises:
from about 5 to about 8 mg astaxanthin; and
from about 250 to about 350 mg of palm fruit extract.

13. The method of claim 10, wherein administering to the subject an effective amount of a composition comprising astaxanthin and palm fruit extract is conducted for a period of from about 4 weeks to about 8 weeks.

14. The method of claim 10, wherein administering to the subject an effective amount of a composition comprising astaxanthin and palm fruit extract is conducted for a period of greater than 4 weeks.

15. The method of claim 10, further including the step of identifying a subject in need of improvement of heart and brain performance.

16. The method of claim 15, wherein identifying a subject in need of improvement of heart and brain performance includes identifying a subject in need of.

17. The method of claim 10, wherein the effective amount is effective to reduce a MCP-1, IL-1B, and/or IL-6 concentration in the subject.

18. A method of simultaneously improving heart and brain performance in a subject comprising:
identifying a subject in need of improvement of heart and brain performance;
administering to the subject in need thereof an effective amount of a composition comprising:
from about 1 mg to about 12 mg of astaxanthin;
from about 125 mg to about 500 mg of palm fruit extract; and
wherein:
the composition is administered to the subject for a period of from about 4 weeks to about 8 weeks;
the effective amount is effective to simultaneously improve heart and brain performance in the subject following administration for the period of at least about 8 weeks; and
the effective amount is effective to improve global mood state in the subject following administration for the period of at least about 8 weeks.

19. The method of claim 18, wherein identifying a subject in need of improvement of heart and brain performance includes identifying a subject in need of.

* * * * *